(12) United States Patent
Tofani et al.

(10) Patent No.: US 11,364,390 B2
(45) Date of Patent: Jun. 21, 2022

(54) APPARATUS FOR TREATING PATHOLOGICAL CELLS

(71) Applicants: Santi Tofani, Burolo (IT); ZHEJIANG UNIVERSITY, Zhejiang (CN)

(72) Inventors: Santi Tofani, Burolo (IT); Xi Chen, Hangzhou (CN); Linqing Yuan, Hangzhou (CN); Kexin Shi, Hangzhou (CN); Chao Yang, Hangzhou (CN); Suchen Bian, Hangzhou (CN); Jinhu Wang, Hangzhou (CN); Kun Zhu, Hangzhou (CN); Min Yang, Hangzhou (CN); Weizhong Gu, Hangzhou (CN); Shiqiang Shang, Hangzhou (CN); Huamei Li, Hangzhou (CN); Zheng Shen, Hangzhou (CN); Can Wang, Hangzhou (CN)

(73) Assignees: Santi Tofani, Burolo (IT); ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/483,862

(22) PCT Filed: Feb. 7, 2018

(86) PCT No.: PCT/IB2018/050765
§ 371 (c)(1),
(2) Date: Aug. 6, 2019

(87) PCT Pub. No.: WO2018/172863
PCT Pub. Date: Sep. 27, 2018

(65) Prior Publication Data
US 2020/0016424 A1    Jan. 16, 2020

(30) Foreign Application Priority Data

Feb. 7, 2017  (CN) .......................... 201710066744.7
Feb. 7, 2017  (CN) .......................... 201710066756.X (51) Int. Cl.
*A61N 2/00*  (2006.01)
*A61N 2/02*  (2006.01)
(Continued)

(52) U.S. Cl.
CPC ............ *A61N 2/004* (2013.01); *A61K 31/282* (2013.01); *A61K 33/243* (2019.01); *A61N 2/002* (2013.01); *A61N 2/02* (2013.01)

(58) Field of Classification Search
CPC .......... A61N 2/004; A61N 2/002; A61N 2/02; A61K 33/243; A61K 31/282
(Continued)

(56) References Cited

U.S. PATENT DOCUMENTS 5,386,837 A * 2/1995 Sterzer .............. A61M 37/0092
                                                                128/898
6,461,289 B1   10/2002 Muntermann
(Continued)

FOREIGN PATENT DOCUMENTS

CN    1053555 A    8/1991
CN    1096968 A    1/1995
(Continued)

OTHER PUBLICATIONS

Motionlabs,Transformer Basics: Information Guide, 2014, Motion Laboratories Inc, pp. 1-14 (attached) (Year: 2014).*
(Continued)

*Primary Examiner* — Sunita Reddy
(74) *Attorney, Agent, or Firm* — Maschoff Brennan (57) ABSTRACT

An electromagnetic field generating apparatus for treating pathological cells, in particular with tumor suppression function. The ratio of static magnetic field to alternating magnetic field is in the range of 0.5-2.5, and the total intensity is in the range up to 100 mT. It provides non-invasive low toxicity and side effects, significantly inhibit-
(Continued)

ing a plurality of tumors, influencing the intracellular superoxide radical content, and promoting cell autophagy. The mechanism of action of the magnetic field is on the electron spin energy levels and consequently on free radical concentration. Additional magnetic field having frequency up to 100 MHz and intensity down to microTesla range can be also used to improve the antitumor efficacy in combination with the static as well as the extremely low frequency electromagnetic field (1-300 Hz) influencing the spin hyperfine resonance. A combination method is also provided of a power-frequency electromagnetic field generating device and a platinum-based medicine.

12 Claims, 7 Drawing Sheets (51) Int. Cl.
  *A61K 33/243* (2019.01)
  *A61K 31/282* (2006.01)
(58) Field of Classification Search
  USPC .................................................. 600/9–15
  See application file for complete search history.

(56) References Cited

U.S. PATENT DOCUMENTS

| | | | |
|---|---|---|---|
| 8,019,414 B2 | 9/2011 | Palti | |
| 8,406,870 B2 | 3/2013 | Palti | |
| 2002/0016582 A1* | 2/2002 | Gray | A61N 1/30 604/500 |
| 2002/0077676 A1* | 6/2002 | Schroeppel | A61N 1/403 607/75 |
| 2003/0095022 A1* | 5/2003 | Boynton | H01F 7/20 335/299 |
| 2005/0267535 A1 | 12/2005 | Tofani | |
| 2007/0142874 A1* | 6/2007 | John | A61N 2/006 607/45 |
| 2007/0161883 A1* | 7/2007 | Ayari | A61N 5/02 600/407 |
| 2007/0173889 A1* | 7/2007 | Rosenspire | A61N 2/004 607/2 |
| 2007/0225766 A1* | 9/2007 | Palti | A61N 1/40 607/2 |
| 2007/0239213 A1* | 10/2007 | Palti | A61N 1/40 607/3 |
| 2008/0319372 A1* | 12/2008 | Palti | A61N 1/326 604/20 |
| 2009/0043346 A1* | 2/2009 | Palti | A61N 1/326 607/2 |
| 2012/0029419 A1 | 2/2012 | Palti | |

FOREIGN PATENT DOCUMENTS

| | | |
|---|---|---|
| CN | 106621050 A | 5/2017 |
| CN | 106902464 A | 6/2017 |
| EP | 1 741 467 A1 | 1/2007 |
| WO | 01/15770 A2 | 3/2001 |
| WO | 2009/153818 A1 | 12/2009 |

OTHER PUBLICATIONS

International Search Report, dated Jun. 1, 2018, corresponding to International Application No. PCT/IB2018/050765.
Artacho-Cordón, Francisco, et al., "Could Radiotherapy Effectiveness Be Enhanced by Electromagnetic Field Treatment?", International Journal of Molecular Sciences, 2013, 14, pp. 14974-14995, ISSN 1422-0067.
Tofani, Santi, "Physics may help chemistry to improve medicine: a possible mechanism for anticancer activity of static and ELF magnetic fields", Oct.-Dec. 1999, Physica Medica, vol. XV, No. 4, pp. 291-294.
Tofani, Santi, "Electromagnetic Field Exposure System for the Study of Possible Anti-Cancer Activity", IEEE Transactions on Electromagnetic Compatibility, Feb. 2002, vol. 44, No. 1, pp. 148-151.
White, Eileen, et al., "The Double-edged Sword of Autophagy Modulation in Cancer", Clin Cancer Res., 15 (17) Sep. 1, 2009, pp. 5308-5316.
Marchesi, Nicoletta, et al., "Autophagy is Modulated in Human Neuroblastoma Cells Through Direct Exposition to Low Frequency Electromagnetic Fields", Journal of Cellular Physiology, 2014, pp. 1-24.
Tofani, Santi, "Electromagnetic Energy as a Bridge between Atomic and Cellular Levels in the Genetics Approach to Cancer Treatment", Current Topics in Medicinal Chemistry, 2015, 15, pp. 572-578.
Barnes, Frank S. et al., "The Effects of Weak Magnetic Fields on Radical Pairs", Bioelectromagnetics 36, 2015, pp. 45-54.
Ronchetto, Flavio, et al., "Extremely Low Frequency-Modulated Static Magnetic Fields to Treat Cancer: A Pilot Study on Patients With Advanced Neoplasm to Assess Safety and Acute Toxicity", Bioelectromagnetics 25, 2004, pp. 563-571.
Hanahan, Douglas, et al., "Hallmarks of Cancer: The Next Generation", Cell 144, Mar. 4, 2011, pp. 646-674.
Booth, Laurence A., et al., The role of cell signalling in the crosstalk between autophagy and apoptosis, Cell Signal, Mar. 2014, 26(3) pp. 549-555.

* cited by examiner

APPARATUS FOR TREATING PATHOLOGICAL CELLS

FIELD OF THE INVENTION

The present invention belongs to the field of physics, biology and medicine and relates to medical devices, especially capable of providing tumor therapeutic electromagnetic fields.

In particular, it provides an apparatus for suppressing malignant cells, especially of the neuroblastoma and nephroblastoma type.

The invention also provides such an apparatus configured to generate a power frequency electromagnetic field in combination with the administration of a platinum-based chemotherapeutic agent.

The invention also provides such an apparatus configured to affect the concentration of oxygen free radicals and for influencing genetic pathway in pathological cells.

The present invention claims conventional priority of already published CN106621050A and CN106902464A, that are here incorporated by reference.

BACKGROUND ART

Low-frequency electromagnetic field frequencies within 300 kilohertz (kHz) can have biological effects related to acting on charged macromolecules and altering their functional status. The inhibitory effect of magnetic fields on tumors has been widely reported (see Artacho-Cordón Francisco et al., 2013, Int J Mol Sci; Tofani S, 2015, Curr Topics in Med Chem).

The European Union and the U.S. FDA have approved the use of a tumor therapeutic magnetic field generating device (Novocure, Israel) for the clinical treatment of multiform glioblastoma, by a magnetic field of 100-300 kHz (see U.S. Pat. Nos. 8,019,414 and, 8,406,870).

A variety of magnetic field applications with tumor suppression effects have also been proposed using strong magnetic fields greater than 0.4 tesla (T) (see Chinese patent application CN90100152) and pulsed magnetic field (see Chinese patent application CN94111668).

Application of a static electromagnetic field generated by DC superimposed with an alternating magnetic field generated by an ultra-low frequency AC has proven to provide effects on the singlet-triplet transition of free-radical lone pair electrons, increasing the chances of level transitions and change of the half-life of free radicals, thereby increasing their biological effects (see Tofani S, 1999, Physica Medica; Barnes F S et al., 2015, Bioelectromagnetics, as well as WO9966987A1).

No significant systemic side effects have been found in low-frequency electromagnetic fields acting on animals and humans (see Tofani S et al., 2002, IEEE Transactions on Plasma Science; Ronchetto F et al., 2004, Bioelectromagnetics). Cell autophagy has important pathophysiological functions. Taku Kokura received the Nobel Prize in Medicine and Physiology for his pioneering contributions in this area. Autophagy has a double-edged sword effect on the fate of cells and can help cells survive or induce apoptosis. It is an important biological feature and therapeutic target for malignant tumors (see White E et al., 2009, Clin Caner Res; Hanahan D et al., 2011, Cell; Booth L A et al., 2014, Cell Signal). Low-frequency magnetic fields have the effect of inducing autophagy (see Marchesi N et al., 2014, Cellular Physiology), but how this affects tumor cell survival and death, as well as specific molecular mechanisms, is not yet known.

As two common childhood malignancies, nephroblastoma is a kidney tumor and neuroblastoma typically occurs in the adrenal gland. They are both derived from undifferentiated or poorly differentiated embryonic cells. Current clinical treatment procedures include surgery, radiation, chemotherapy and stem cell transplantation. The clinical outcomes depend on the staging of the patients and the differential state of tumor cells. For patients with relapse and metastasis, anaplastic tumor cells are usually resistant to conventional radio- and chemo-therapies, and there is still lack of treatment options, thus the fatality rate remains high. Moreover, the surviving patients frequently suffer from side effects as a consequence of radiation and cytotoxic drugs. There is always demand for development of novel therapeutic options to treat the highly malignant tumors and to reduce the side effects of conventional therapeutics.

SUMMARY OF THE INVENTION

It is an object of the present invention to provide an apparatus for successfully treating and suppressing malignant cells of the neuroblastoma and nephroblastoma type using non-invasive application of static and alternating electromagnetic fields.

According to a first aspect of the invention, an apparatus for treating pathological cells, in particular of neuroblastoma and nephroblastoma type, comprises a workspace configured to receive a target body, at least one set of coils arranged to irradiate a static electromagnetic field in said workspace and also arranged to irradiate an alternating magnetic field in said workspace, a control unit arranged to supply selectively current to said at least one set of coils in such a way to irradiate in said workspace a static electromagnetic field and an alternating magnetic field for predetermined time intervals T1, T2, T3, . . . Tn, said control unit arranged to supply selectively current to said at least one set of coils in such a way to irradiate in said workspace said static electromagnetic field and an alternating magnetic field superimposed to each other with a maximum superimposed strength of 100 mT and ratio of static electromagnetic field to alternating magnetic field is in the range of 0.5-2.5, said static electromagnetic field having an intensity selected in such a way that said static electromagnetic field and alternating magnetic field superimposed to each other have always a positive strength.

Preferably, said control unit keeps the total magnetic field at a same overall strength in said workspace, said overall strength comprised within a range of 1.0-7.0 mT, wherein the average strength is comprised between 4 and 6 mT, in particular the average strength is 4.5-5.5 mT, preferably 5.1 mT.

According to a preferred embodiment, said set of coils is selected from the group consisting of
- a single set of coils in which a voltage supply is applied superimposing a static DC supply and an alternating AC supply,
- a first set of coils arranged to irradiate a static electromagnetic field in said workspace and a second set of coils arranged to irradiate an alternating magnetic field in said workspace.

The patient can be arranged to move relatively to the single set of coils or multiple set of coils.

Advantageously, said control unit is configured to supply selectively current to said set of coils in each time interval T1-Tn according to a predetermined voltage scheme, according to which in each time interval T1-Tn the DC voltage applied to said set of coils is in a voltage range between 1-5 mV, resulting in a static electromagnetic field in a strength range between 1-5 mT, the AC voltage applied to said set of coils is in an average voltage range between 1-5 mV, resulting in an alternating magnetic field with an average strength range of 1-5 mT.

In particular, a power frequency electromagnetic field generating apparatus with tumor suppression function, comprises a power frequency power source, two autotransformers, two diode bridges, two groups of coils, an irradiation part, a voltage detection part, a magnetic field detection part, temperature measurement components and terminal computer components.

In a possible embodiment, said AC supply is provided at a frequency of 50/60 Hz, through the DC and AC autotransformer constantly changing voltage, thus generating superimposed static and alternating magnetic fields in the irradiated parts.

In possible advantageous embodiments, the magnetic alternating field with tumor suppression effect of the present invention can provide a frequency in the range up to 100 MHz, the ratio of static electromagnetic field to alternating magnetic field always in the range of 0.5-2.5, and the total strength is in the range up to 100 mT.

The invention is a special power frequency electromagnetic field generating device and application mode, which is designed rationally and can act on the organism, has the advantages of non-invasive low toxicity and side effects, significantly inhibits a plurality of tumors, and can influence the intracellular superoxide radical content, and promote cell autophagy.

The hypnotized mechanism of action is the influence of the magnetic field on the electron spin energy levels and consequently on the free radicals concentration through the Zeeman effect. Additional magnetic field having frequency up to 100 MHz and strength down to micro Tesla range may be also used to improve the antitumor efficacy of the treatment due to the combine effect between the MHz field and the static as well as the extremely low frequency magnetic field (1-300 Hz) on the spin hyperfine resonance. According to an aspect of the invention, an apparatus configured to generate a power frequency electromagnetic field in combination with the administration of a platinum-based chemotherapeutic agent is provided.

The apparatus can therefore provide a combination treatment of a power-frequency electromagnetic field generating device and a platinum-based chemotherapeutic agent.

The power frequency 50/60 Hz power supply is used to constantly change the voltage through the direct current and alternating current auto-transformers, internal generated superimposed static and alternating magnetic fields, the average loading magnetic field strength of 4.5 to 5.5 millitesla, in particular 5.1 millitesla, irradiated components on the exposure to the total daily irradiation time of 60-120 minutes, the platinum-based chemotherapeutic agent applied to the irradiated components.

The device has the advantages of reasonable design, unique frequency, static and alternating magnetic fields loaded at the same time, the magnetic field strength generated by the device is uniform, highly controllable and convenient to implement; the interference of the illuminated object is small and non-invasive; the in vitro and in vivo experiments confirmed that the tumor therapeutic electromagnetic field combined with platinum-based chemotherapy drugs has the following beneficial effects: it can enhance the efficacy of platinum-based chemotherapy drugs and magnetic field alone, it can have a significant inhibition of a variety of tumors; it can reduce the dose of cisplatin and reduce side effects thereof.

It is an object of the present invention to provide a power frequency electromagnetic field generating device with tumor suppressing effect comprising a magnetic field generating unit providing an application sequence of ultra-low frequency, low strength, capable of acting on a living body and generating a specific biological effect. The application sequence has tumor inhibitory effect both in vitro and in vivo.

In possible embodiments of the present invention the same exposure apparatus previous established [Tofani et al., 2001 Bioelectromagnetics; Tofani, 2002 IEEE Plasma Science; Tofani, 2002 Bioelctromagnetics] can be used. The characteristics of the MF generated by this embodiment have been reported in detail [Tofani, 2002, IEEE Transaction on EMC]. Here we have selected specific exposure conditions slightly different from that previously established. In the experiments carried out according to the invention, the time-average strength of the MF was slightly different from the previous studies, 5.09 mT instead of 5.5 mT. This is due to the modification of the time duration of each of the many rounds constituting one MF treatment session. The present exposure conditions result to be effective in new cancer types (neuroblastoma and nephroblastoma) before not considered In a possible embodiment the power frequency electromagnetic field generating device comprises a power frequency power source, a first autotransformer (AC/AC), a second autotransformer (DC), a first diode bridge and a second diode, a first set of coils, a second set of coils, an irradiation part, a voltage detection part, a magnetic field detection part, a temperature measurement part and a terminal computer.

In a possible embodiment, the power frequency power supply can be respectively connected with one end of the first autotransformer and the second autotransformer, said ends of the first autotransformer and the second autotransformer are respectively connected with the first diode bridge and the second diode bridge, said end of the first diode bridge is connected with the first group of coils. Said end of the second diode bridge is connected with the second group of coils, the irradiation component is placed between the first group of coils and the second group of coils, one end of the voltage detection component is respectively connected with the first group of coils and the second group of coils and said end is connected with the terminal computer.

In such embodiment, one end of each of the magnetic field detection component and the temperature measurement component can be respectively connected with the irradiation component, and said end of the magnetic field detection component and the temperature measurement component are respectively connected with the terminal computer.

Two types of irradiation components can be provided, a first one is a cell irradiation platform designed for the cell culture plate and the culture plate, which consists of a first plate, a second plate, and a stage between the two separators. The cell culture plate is placed on a stage with a spacing d, which can be for example of 12.9 cm between the two separators. The height of the stage is adjustable to ensure that the bottom of the cell culture plate is located in the middle of the irradiated area. A second irradiation unit, in the experimental prototype designed for animal irradiation platform, designed primarily for mice, consisted of a first separator, a second separator, and six animal irradiation cells located between the two separators and arranged in an animal irradiation chamber, the parts including a front baffle, a rear baffle, an intermediate baffle, and four chamber baffles. Four front baffles and rear baffles can provide drilled multiple ventilation holes, so as to avoid animal hypoxia. The first and second separators can be spacing 12.9 cm from each other and the six irradiation cells can be located in the middle of the irradiation chamber so that each round of irradiation can treat 6 mice. Irradiation components can be made of transparent resin plate material, so that they can be cleaned with UV disinfection.

According to a particular aspect of the present invention a method of magnetic field application using the device, by: using 50/60 Hz frequency power supply, through the DC and AC autotransformer constantly changing the voltage, thus generating superimposed static (from the DC) and alternating (from AC) electromagnetic field within the irradiated components;

applying a voltage scheme in each time period T1-Tn to generate different magnetic field strengths in a total of eight time periods T1-T8 namely:

T1—a DC voltage of 3 mV, to generate a static electromagnetic field strength of 2.97 mT, an AC average voltage of 1.5 mV, to generate an average alternating magnetic field strength of 1.48 mT;

T2—a DC voltage of 4 mV to generate a static electromagnetic field strength of 3.95 mT, an AC average voltage of 2.5 mV, to generate an alternating magnetic field average strength of 2.47 mT;

T3—a DC voltage of 3 mV, to generate a static electromagnetic field strength of 2.97 mT, an AC average voltage of 1.5 mV, to generate an alternating magnetic field average strength of 1.48 mT;

T4—a DC voltage of 4 mV, to generate a static electromagnetic field strength of 3.95 mT, an AC average voltage of 2.5 mV, to generate an alternating magnetic field average strength of 2.47 mT;

T5—a DC voltage of 3 mV to generate a static electromagnetic field of 2.97 mT; an AC average voltage of 1 mV, to generate an alternating magnetic field average strength of 1.08 mT;

T6—a DC voltage of 4 mV into generate a static electromagnetic field strength of 3.95 mT, an AC average voltage of 1.5 mV, to generate an alternating magnetic field average strength of 1.48 mT;

T7—a DC voltage of 3 mV, to generate a static electromagnetic field strength of 2.97 mT, an AC average voltage of 1 mV, to generate an alternating magnetic field average strength of 1.08 mT;

T8—a DC voltage of 4 mV, to generate a static electromagnetic field strength of 3.95 mT, an AC average voltage of 1.5 mV, to generate an alternating magnetic field average strength of 1.48 mT.

The total magnetic field strength is the same at different positions inside the irradiated region, the average magnetic field strength is 5.09 mT from T1 to T8; each time the T1-T8 time is changed, the voltage is continuously irradiated for 3.5-10 minutes, irradiation time accumulated 30-90 minutes, 2-4 rounds of daily irradiation, the total daily irradiation time of 60-120 minutes for cells and animals.

The electromagnetic field with tumor suppression effect described in this advantageous configuration has a frequency in the range of 30-300 Hz, a total strength of static (direct current) and alternating (alternating current) electromagnetic fields in the range of 1-10 mT, static (direct current) and alternating (alternating current) strength ratio of electromagnetic field is in the range of 0.5-2.5.

The apparatus can be configured to provide a magnetic field effect time, each time the voltage changes continued irradiation 3.5-10 minutes, each round of irradiation time 30-90 minutes, the total daily irradiation time 60-120 minutes, the device and method provide application on a variety of tumors having a significant inhibitory effect in vitro and in vivo, magnetic field can increase the content of superoxide radicals and promote autophagy.

The electromagnetic field generating device and the application method described in the present invention have significant in vitro and in vivo inhibitory effects on various tumors. The magnetic field can increase the intracellular superoxide radical content and promote cell autophagy. In vitro cell culture experiments and cell viability experiments showed that the generated magnetic field can inhibit a variety of tumor cell growth, including nephroblastoma, neuroblastoma, breast cancer, colorectal cancer and other cells; in vitro experiments can be effective Inhibits the growth and metastasis of colorectal and breast cancers.

The invention has the following beneficial effects: (1) the device has a reasonable design, adopts a unique power frequency and is convenient to implement; (2) the static electromagnetic field generated by the direct current is superposed with the alternating magnetic field generated by the alternating current and can affect free radicals in the magnetic field and enlarge its biological effect; (3) uniform strength of the magnetic field in the irradiated part; (4) easy operation, application scheme can be realized by changing the voltage; (5) continuous monitoring of the relevant voltage, magnetic field strength, Highly controlled; (6) placed in the irradiated parts of the organism suffered little interference, no trauma; (7) has a significant inhibitory effect on a variety of tumors, and low side effects; (8) enhancement.

According to a particular object of the present invention a combination method of a power frequency electromagnetic field generating device and a platinum-based drug is provided, whose combined is greater than a platinum-based drug or an electromagnetic field are used alone. The above exposure apparatus was found to exert synergistic effect with chemotherapeutic agent cisplatin in a Luis lung carcinoma (Tofani 2003 Pharmacological Research), in the present invention, we show that specific sequences of the old magnetic fields treatment are able to exert synergistic activity with cisplatin in a different tumor, that is nephroblastoma.

The combination method of the power frequency electromagnetic field generating device and the platinum-based medicine provided by the present invention is realized through the following steps:

The construction of power frequency electromagnetic field generator, using frequency 50/60 Hz power supply, through the DC and AC autotransformer constantly changing voltage, thus generating superimposed static (from DC) and alternating (from AC) electromagnetic field inside the irradiated parts, the overall average strength of the magnetic field can be for example 5.09 mT, and the total irradiation time per day for irradiated components is 60-120 minutes; the exposure of the platinum-based drug to the irradiated components, the platinum-based drug The use of cisplatin, carboplatin, oxaliplatin and other platinum-based chemotherapeutic agents, use and dosage: in vitro concentration of 500 nM, dosing once a day, the body dose of 20 mg/kg, administered three times a week, this is the lower dose selected in the cisplatin effective dose range.

The apparatus of the invention provides that the combination of the tumor therapeutic electromagnetic field and the platinum-based chemotherapeutic drugs such as cisplatin can enhance antitumor effect through in vitro and in vivo experiments instead of simple superposition.

Therefore, the present invention has the following beneficial effects: (1) The device uses a unique power frequency and loads static (direct current) and alternating (alternating current) electromagnetic fields at the same time, and the magnetic field strength generated by the device is uniform and highly controllable; 2) The organism is less disturbed and non-invasive; (3) It can enhance the curative effect of platinum-based chemotherapy drugs and has significant inhibitory effect on various tumors; (4) It can reduce the dose of cisplatin and reduce the side effects.

According to a particular aspect of the invention, magnetic fields at much higher frequency (MHz magnitude, for example between 100 kHz and 100 MHz) used in combination with static electromagnetic fields can also have importance in influencing the spin states and then the correspondent chemical reactions. In fact, multiple interactions in which weak magnetic fields (strength on the order micro Tesla, or µT) at higher frequency can change the population distribution in the various spin states, among them the electron-nuclear hyperfine interaction. External static in combination with high frequency magnetic fields can alter radical pair spin dynamics by Zeeman and HFI resonance effects, and thereby change the relative yields of reaction products that derive, alternatively, from singlet and triplet radical pair states. Many biological molecules exhibit hyperfine splitting constant that range from 0.1 to 35 MHz, so fields of this frequency may be used to influence hyperfine coupling resonance. Magnetic fields at this higher frequency and very low strength have been used, together with static electromagnetic fields, to influence hyperfine resonance decreasing the intracellular superoxide concentration to selectively increase rat pulmonary arterial smooth muscle cells proliferation (Tofani S., 2018, Cancer Treatment, Intech, in press).

BRIEF DESCRIPTION OF THE DRAWINGS

The invention will be now shown with the following description of its exemplary embodiments, exemplifying but not limitative, with reference to the attached drawings in which.

DETAILED DESCRIPTION

The present invention is further described below with reference to the accompanying drawings and embodiments.

Embodiment 1

Figure 1:
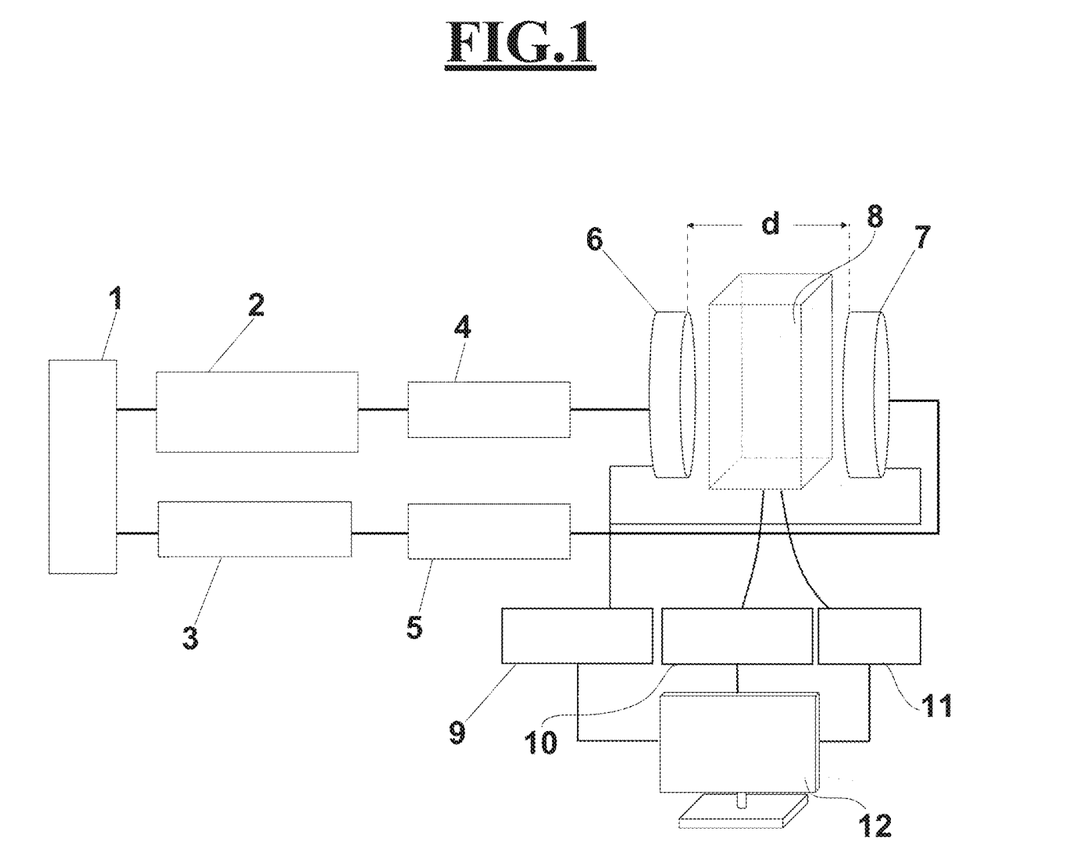
FIG. 1 is a schematic structural view of the electromagnetic field generating device of the present invention.

The embodiment provides a power frequency electromagnetic field generating device with tumor suppression function, which comprises a commercial power supply 1, a first autotransformer 2 (AC AC), a second autotransformer 3 (DC) A first diode bridge 4, a second diode bridge 5, a first group of coils 6, a second group of coils 7, an irradiation unit 8, a voltage detection unit 9, a magnetic field detection unit 10, a temperature measurement unit 11 and A terminal computer 12, a power frequency power supply 1 is respectively connected with one end of the first autotransformer 2 and the second autotransformer 3, said end of the first autotransformer 2 and the second autotransformer 3 are respectively connected with the first diode The bridge 4 is connected to the second diode bridge 5, said end of the first diode bridge 4 is connected to the first group of coils 6, and said end of the second diode bridge 5 is connected to the second group of coils 7, the irradiation unit 8 is disposed between the first set of coils (6) and the second set of coils (7), one end of the voltage detection unit 9 is connected to the first set of coils (6) and the second set of coils (7), respectively, and said end is connected to the terminal computer 12, one end of each of the magnetic field detecting part 10 and the temperature measuring part 11 is respectively connected with the irradiating part 8, 12 is connected to the computer.

Figure 2:
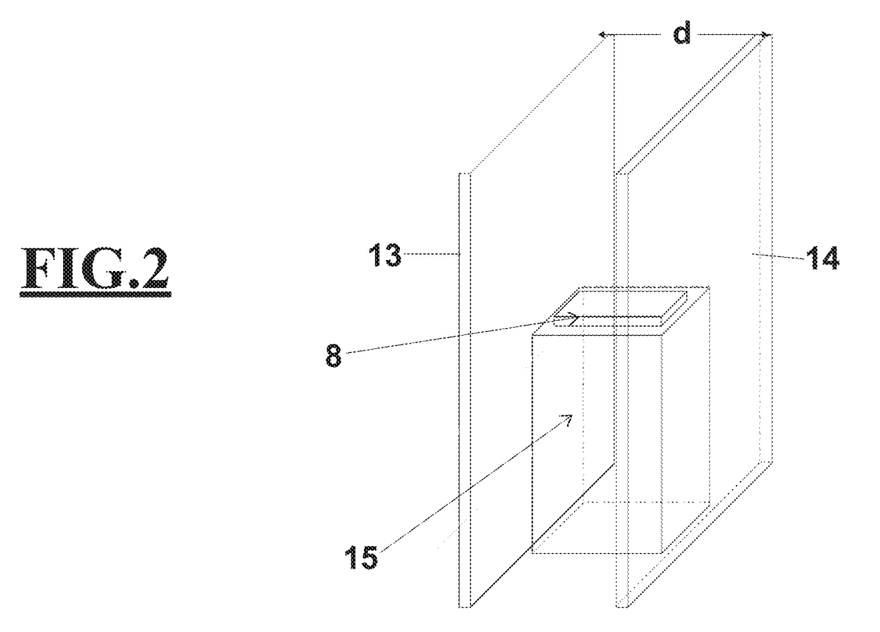
FIG. 2 is a schematic diagram of a cell irradiation platform placed in a magnetic field, one of the irradiation components of the device of the present invention.

There are two types of irradiation components 8, the first one is a cell irradiation platform designed for the cell culture plate and the petri dish, and consists of a first partition plate 13, a second partition plate 14, and a stage 15 located between the two partition plates. The cell culture plate is placed on the stage. The distance d between the first partition plate 13 and the second partition plate 14 can be for example 12.9 cm. The height of the stage can be adjustable to ensure that the bottom of the cell culture plate is located in the middle of the irradiation zone.

Figure 3:
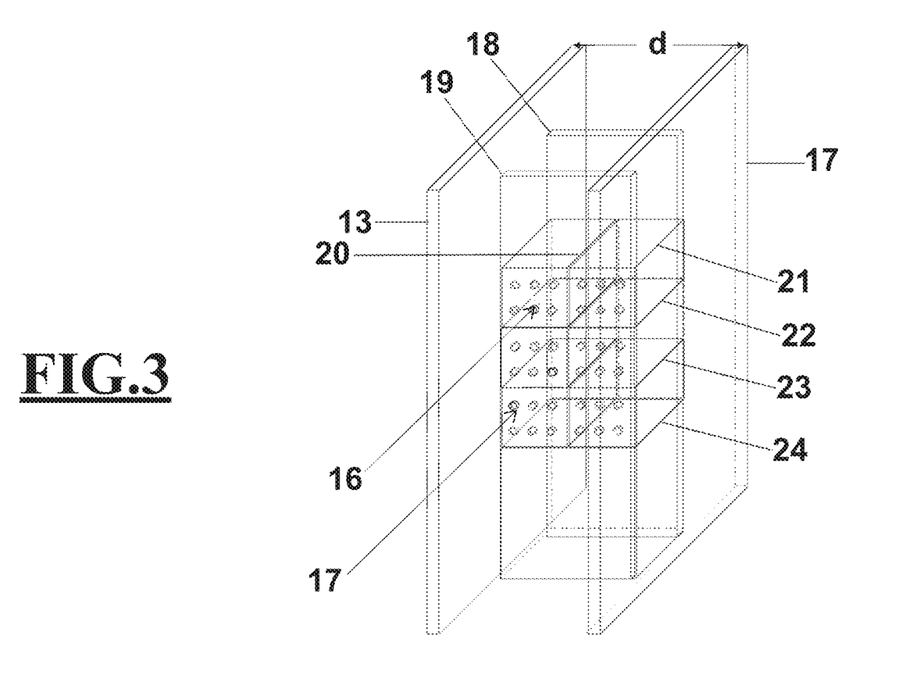
FIG. 3 is a schematic diagram of an animal irradiation platform placed in a magnetic field, which is the second part of the irradiation device of the present invention.
Figure 11:
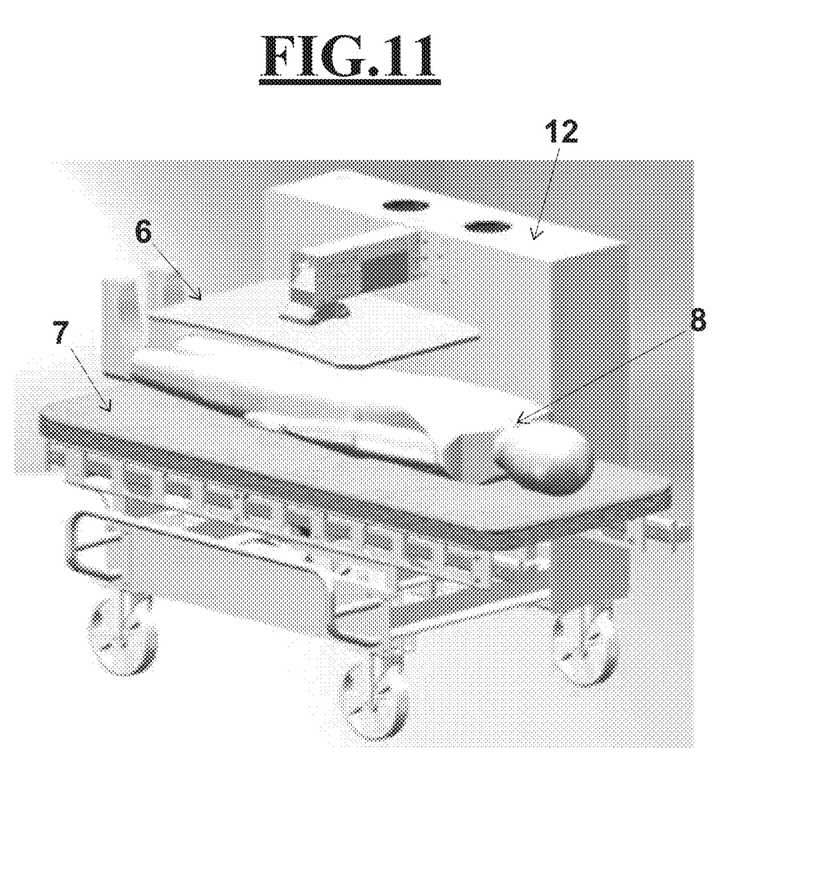
FIGS. 11 and 12 show perspective views of possible embodiments of the apparatus according to the invention.
Figure 12:
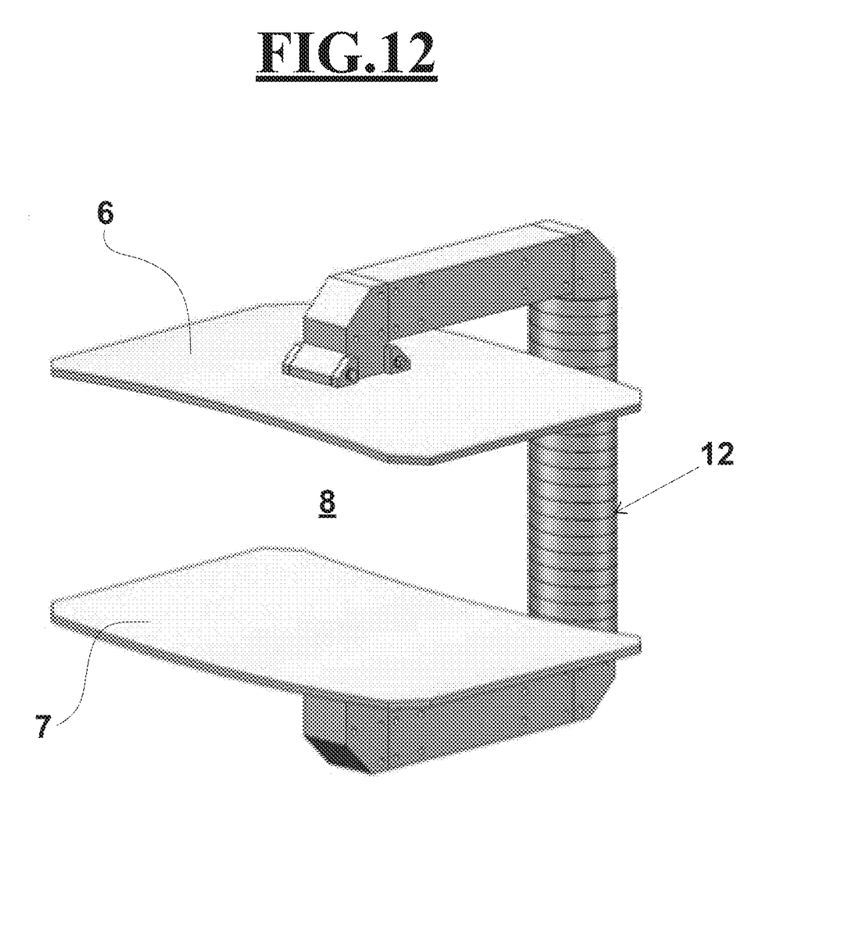

The second irradiation unit 8 can be an animal irradiation platform and is mainly designed for mice. The irradiation unit can be broadly defined as a workspace 8. Of course, a design for therapeutic application can be provided, as depicted in FIGS. 11 and 12.

The irradiation unit 8 can be composed of a first partition plate 13, a second partition plate 14 and six animal irradiation chambers 16 arranged each between the two partition plates to form an animal irradiation chamber 16. The components of the irradiation chamber 16 include a front baffle 18, a back baffle 19, a middle baffle 20, a small baffle 21, a small baffle 22, a small baffle 23 and a small baffle 24, wherein the front baffle Plate 18 and the back baffle 19 are drilled by a plurality of small holes 17 which act as a vent to avoid animal hypoxia. Partition plate 13 and partition plate 14 can be 12.9 cm wide, and six irradiation chambers 16 are located in the middle of the irradiation area, so that six mice can be treated per cycle of irradiation. The irradiation unit 8 can be made of transparent resin, which can be cleaned and disinfected with ultraviolet light.

Figure 4:
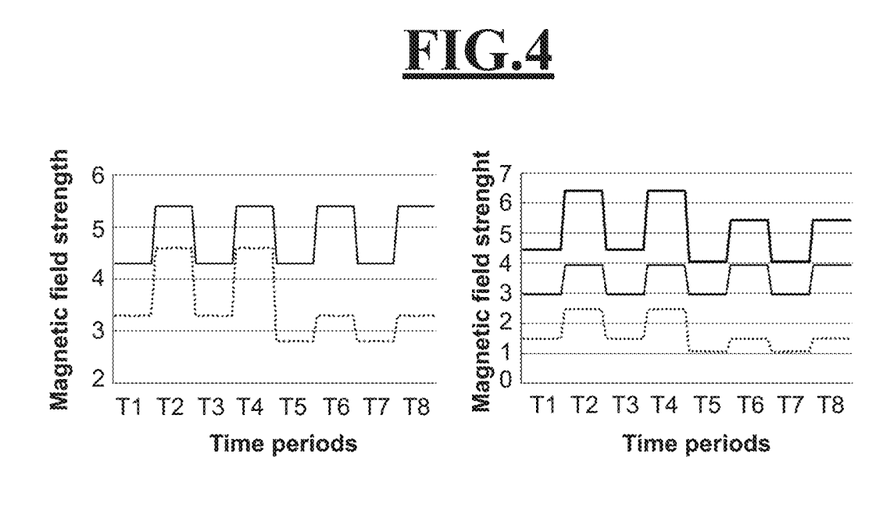
FIG. 4 shows the main parameters of the electromagnetic field application method according to the present invention, that is, the DC and AC voltage variations and the corresponding electromagnetic field intensities are shown. The AC voltage is shown as an average.

A specific magnetic field application method can adopt a scheme as shown in FIG. 4, adopting a power frequency of 50/60 Hz, continuously changing the voltage through the direct current and the alternating current autotransformer, thereby generating the static and alternating field superposition electromagnetic field inside the irradiating component A specific voltage scheme in each time period T1-Tn is applied to generate different magnetic field strengths in a total of eight time periods T1-T8 namely:

- T1—a DC voltage of 3 mV, to generate a static electromagnetic field strength of 2.97 mT, an AC average voltage of 1.5 mV, to generate an average alternating magnetic field strength of 1.48 mT;
- T2—a DC voltage of 4 mV to generate a static electromagnetic field strength of 3.95 mT, an AC average voltage of 2.5 mV, to generate an alternating magnetic field average strength of 2.47 mT;
- T3—a DC voltage of 3 mV, to generate a static electromagnetic field strength of 2.97 mT, an AC average voltage of 1.5 mV, to generate an alternating magnetic field average strength of 1.48 mT;
- T4—a DC voltage of 4 mV, to generate a static electromagnetic field strength of 3.95 mT, an AC average voltage of 2.5 mV, to generate an alternating magnetic field average strength of 2.47 mT;
- T5—a DC voltage of 3 mV to generate a static electromagnetic field of 2.97 mT; an AC average voltage of 1 mV, to generate an alternating magnetic field average strength of 1.08 mT;
- T6—a DC voltage of 4 mV into generate a static electromagnetic field strength of 3.95 mT, an AC average voltage of 1.5 mV, to generate an alternating magnetic field average strength of 1.48 mT;
- T7—a DC voltage of 3 mV, to generate a static electromagnetic field strength of 2.97 mT, an AC average voltage of 1 mV, to generate an alternating magnetic field average strength of 1.08 mT;
- T8—a DC voltage of 4 mV, to generate a static electromagnetic field strength of 3.95 mT, an AC average voltage of 1.5 mV, to generate an alternating magnetic field average strength of 1.48 mT.

The total magnetic field strength is the same at different positions inside the irradiated region, the average magnetic field strength is 5.09 mT from T1 to T8; each time the T1-T8 time is changed, the voltage is continuously irradiated for 3.5-10 minutes, Irradiation time accumulated 30-90 minutes, 2-4 rounds of daily irradiation, the total daily irradiation time of 60-120 minutes for cells and animals.

Embodiment 2

Effect of the Present Invention on Cultured Nephroblastoma Cell G401. Using the apparatus shown in FIG. 1 and FIG. 2, the cells were treated according to the protocol described in FIG. 4, and each time the voltage was changed for 3.5 minutes, the action time per round was about 30 minutes, four times a day, a total of 2 hours of electromagnetic field irradiation time; negative control group cells placed in the electromagnetic field coil is placed between the platform, the same time; positive control cisplatin (Jiangsu Howson Pharmaceutical Co., Ltd. Company) at a concentration of 500 nM administered once daily.

Specific Implementation Process.

Figure 5:
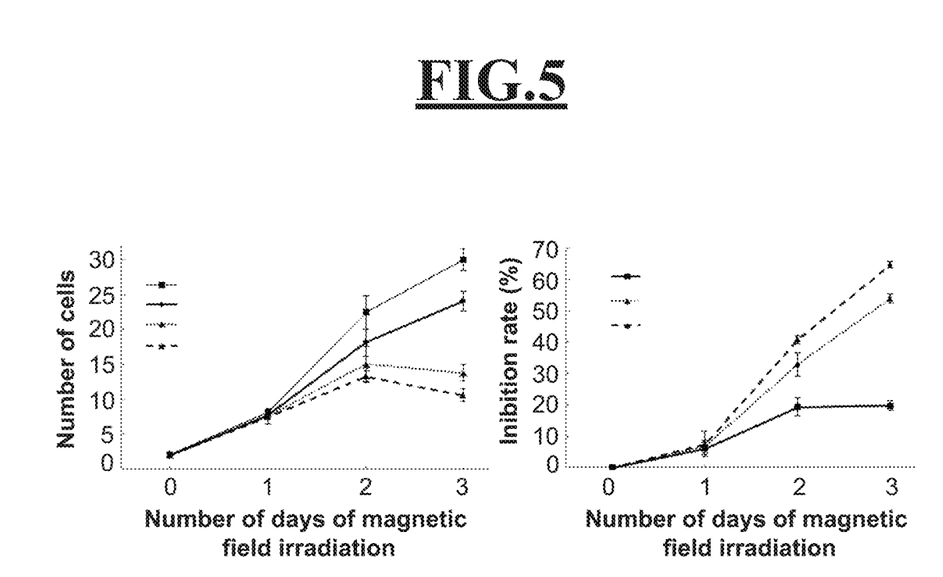
FIG. 5 is a graph showing the inhibitory effect of G401 against nephroblastoma cells of the present invention.
Figure 7:
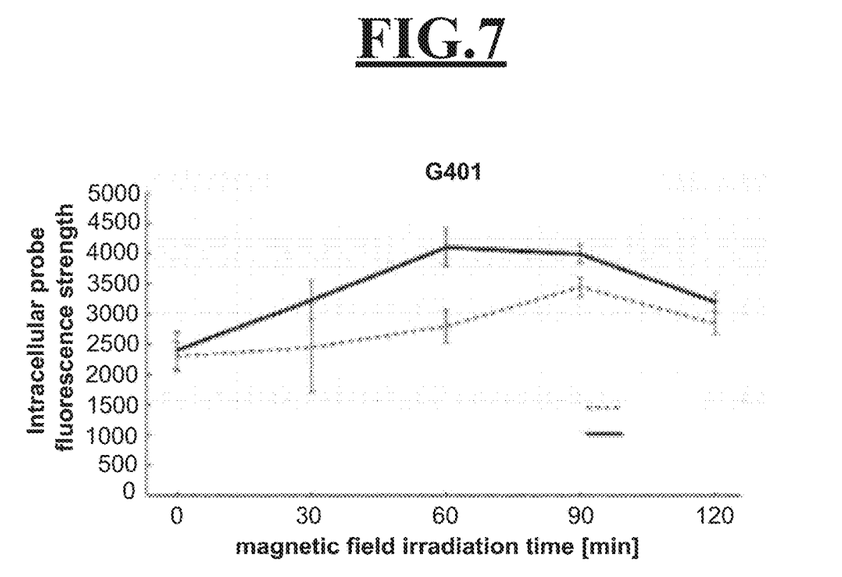
FIG. 7 is an effect diagram of changing the content of superoxide radical in G401 of the nephroblastoma cell by the electromagnetic field in the present invention.

Cell Lines and Methods of Culture: Nephroblastoma cells G401, adherent cells, cultured in a 37° C. incubator with 5% carbon dioxide and saturated steam in McCoy medium with 10% fetal bovine serum;

Major equipment: power frequency electromagnetic field device, cell incubator, living cell counter, multi-functional microplate reader;

Main reagents: CCK8 kit, fluorescent probe DCFH-DA, BCA kit, 40% acrylamide gel stock solution, Tris base, TEMED, SDS, protease inhibitors, protein standards, HRP chemiluminescence detection kit;

Antibodies: primary antibody including LC3, GAPDH, p62, anti-mouse and anti-rabbit HRP conjugated secondary antibody;

Cell viability test: The nephroblastoma cell line G401 was seeded in a 6-well plate at a density of $1\times10^5$ cells/well, and three replicate wells per treatment condition. The control group, the irradiation group and the cisplatin group were treated according to the above protocol Were dealt with, the day before the collection of cells treated with a living cell counter count, calculated according to reading the number of cells to make cell proliferation curve and electromagnetic field inhibition curve;

Statistical analysis: Each irradiation conditions were repeated 3 times, each time three holes, the results were mean±standard error, the results do T test, with $P<0.05$ as a significant difference in indicators;

As shown in FIG. 5, the left panel shows the cell proliferation curve, where the X-axis is the number of days of magnetic field irradiation, the Y-axis is the number of cells, the curve one is the cell proliferation curve of the control group, the curve two is the cell proliferation curve of the irradiation group, As the positive control group, cell proliferation curve of cisplatin group; the right side of the figure is the cell inhibition curve, where the X-axis magnetic field irradiation days, Y axis inhibition rate (%), the curve for the irradiation group cell inhibition rate curve Cisplatin group cell inhibition rate curve; The results showed that irradiation group cells slowed down, the inhibition rate increased;

Determination of superoxide radical content: The nephroblastoma cells G401 were seeded into 96-well plates at a density of $1\times10^4$ cells/well, and each treatment condition was 3 wells. The irradiation group was treated as shown in FIG. 4, Each round of time 30 minutes, the control group placed in the electromagnetic field coil is not placed between the stage, a total of four rounds of treatment, a total of 120 minutes irradiation time, after each round of treatment with fluorescent probe DCFH-DA (10 μM) Incubation in the incubator for 20 minutes, incubated with PBS after washing did not enter the cell probe, with a multi-function microplate reader detection, excitation wavelength 488 nm, absorption wavelength 525 nm, respectively, read the fluorescence strength values of each group; as shown in FIG. 7, Where the X-axis is the magnetic field irradiation time, the Y-axis is the intracellular probe fluorescence strength, that is the relative content of superoxide free radicals, the curve one is the relative content of superoxide free radicals in the control cells, and the curve two is the irradiation group The relative content of superoxide free radicals in the cells showed that the intracellular superoxide radicals in the irradiation group were higher than the control group after receiving a round of 30-minute irradiation, and continued until 120 minutes To a level close to the control group, the result said Clearly this magnetic field application method can indeed increase the content of free radicals in the cell, and markedly rapid, time in 1 hour.

Figure 8:
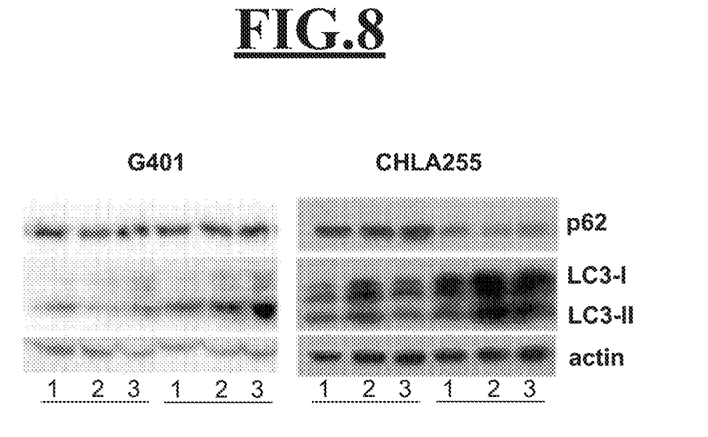
FIG. 8 is a schematic diagram of the electromagnetic field inhibition of tumor cells G401 and CHLA255 in the present invention, including the development of autophagy-related protein bands by HRP chemiluminescence.

Immunoblotting experiments: Cells were centrifuged after treatment, washed in PBS, suspended in prechilled RIPA buffer (added with protease and phosphorylase inhibitor), and then subjected to BCA method for protein quantification, and the proteins were separated by SDS-PAGE gel electrophoresis, Each hole sample amount of 20 μg, with the appropriate antibody for immunization hybridization, HRP chemiluminescence method of protein bands, as shown in FIG. 8, p62 decreased after irradiation, LC3-II increased, indicating that irradiation can induce G401 Autophagy.

Embodiment 3

The present invention acts on cultured neuroblastoma cells, CHLA255, using the apparatus shown in FIG. 1 and FIG. 2, and the cells were treated according to the protocol as shown in FIG. 4, and each time the voltage was changed for 3.5 minutes and the action time per round was about 30 Minutes, 4 days a day, a total of 2 hours of electromagnetic field irradiation time; negative control group cells placed in the coil between the electromagnetic field application platform between the same time; positive control for cisplatin (Jiangsu Howson Pharmaceutical Co., Ltd.), Administered at a concentration of 500 nM once daily.

A specific implementation process was the following.

Figure 6:
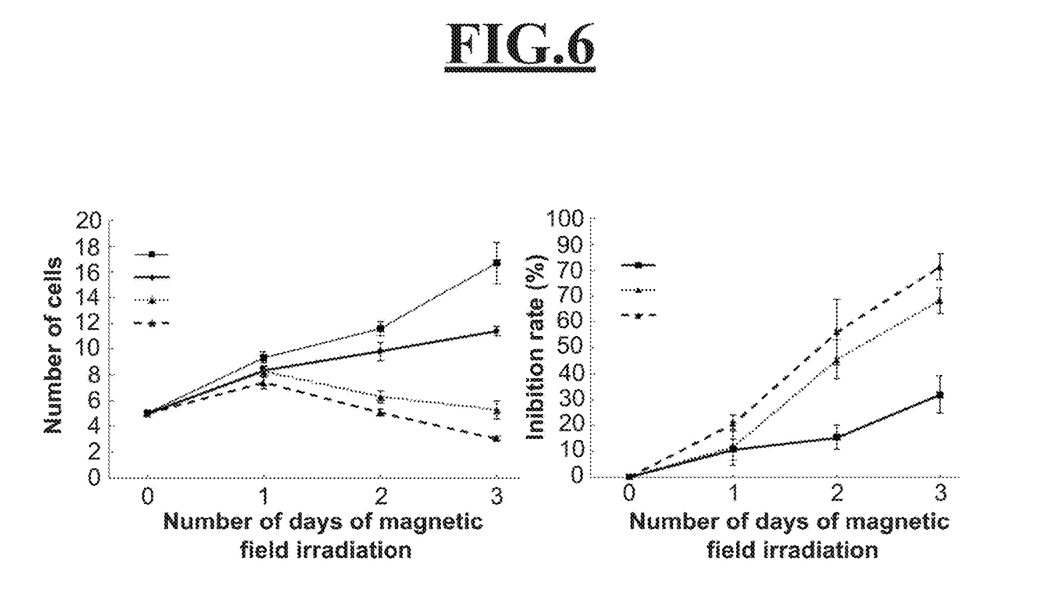
FIG. 6 shows the inhibitory effect of the invention on neuroblastoma cell line CHLA255.

Cell lines and culture methods: Neuroblastoma cells CHLA255, adherent cells, cultured in 37° C. incubator with 10% fetal bovine serum in IMDM medium containing 5% carbon dioxide and saturated water vapor;

Major equipment: power frequency electromagnetic field device, cell incubator, live cell counter;

Main reagents: CCK8 kit, BCA kit, 40% acrylamide gel storage solution, Tris base, TEMED, SDS, protease inhibitors, protein application standards, HRP chemiluminescence detection kit;

Antibodies: primary antibody including LC3, GAPDH, p62, anti-mouse and anti-rabbit HRP conjugated secondary antibody;

Cell Viability Assay: The neuroblastoma cells, CHLA255, were seeded in 6-well plates at a density of $1 \times 10^5$/well with 3 replicate wells per treatment condition. Control, radiation and cisplatin groups were treated as described above Were dealt with, the day before the collection of cells treated with a living cell counter count, calculated according to reading the number of cells to make cell proliferation curve and electromagnetic field inhibition curve;

Statistical analysis: Each irradiation conditions were repeated 3 times, each time three holes, the results were mean±standard error, the results do T test, with $P<0.05$ as a significant difference in indicators;

As shown in FIG. 6, the left panel shows the cell proliferation curve, in which the X-axis is the days of magnetic field irradiation, the Y-axis is the cell number, the curve one is the cell proliferation curve of the control group, the curve two is the cell proliferation curve of the irradiation group, Is the cell proliferation curve of cisplatin group; the right graph is the cell inhibition curve, wherein the X-axis is the days of magnetic field irradiation, the Y axis is the inhibition rate (%), the curve is the cell inhibition rate curve of irradiation group, Platinum group cell inhibition rate curve, the figure results showed that irradiation group cells slowed down, the inhibition rate increased;

Immunoblotting experiments: Cells were centrifuged, washed in PBS, suspended in prechilled RIPA buffer (protease and phosphorylase inhibitor added), and protein quantified by BCA method, and the proteins were separated by SDS-PAGE gel electrophoresis. As shown in FIG. 8, p62 decreased and LC3-II increased after irradiation, indicating that irradiation can induce CHLA255 cells to self-immunize.

Example 4

A magnetic field generating device of the present invention can be combined with a platinum-based chemotherapeutic agent treatment.

The method is implemented by the following steps: constructing a power frequency electromagnetic field generating device, adopting a power frequency of 50/60 Hz, continuously changing the voltage through a DC-AC autotransformer to generate superposition static (by DC) and alternating (by AC) electromagnetic field with an average magnetic field for example of 5.09 milliTesla (mT) for a total irradiation time of 60-120 minutes per day for the irradiated parts on the irradiated part; applying the platinum-based drug to the irradiated part exposure, platinum-based chemotherapeutic agents selected cisplatin, carboplatin, oxaliplatin and other platinum-based chemotherapeutic agents, use and dosage: in vitro concentration of 500 nM, dosing once a day, the body dose of 20 mg/kg, each Weekly dosing 3 times, this is the lower dose selected in the effective dose range of cisplatin.

The power frequency electromagnetic field generator comprises a power frequency power source 1, a first autotransformer 2 (AC AC), a second autotransformer 3 (DC DC), a first diode bridge 4, a second A diode bridge 5, a first group of coils 6, a second group of coils 7, an irradiation unit 8, a voltage detection unit 9, a magnetic field detection unit 10, a temperature measurement unit 11 and a terminal computer 12. The commercial power supply 1, One end of the first autotransformer 2 and the second autotransformer 3 are connected, said end of the first autotransformer 2 and the second autotransformer 3 are respectively connected with the first diode bridge 4 and the second diode electrification The bridge 5 is connected, said end of the first diode bridge 4 is connected to the first set of coils (6), said end of the second diode bridge 5 is connected to the second set of coils (7), the irradiation member 8 is placed on the first Between the set of coils 6 and the second set of coils (7), one end of the voltage detection unit 9 is connected to the first set of coils (6) and the second set of coils (7), respectively, and said end is connected to the terminal computer 12. Each of the magnetic field detection unit 10 and the temperature measurement unit 11 One end of each is connected to the irradiation unit 8, and said end of each is connected to the terminal computer 12, respectively.

In FIG. 3, there are two types of irradiation components 8, the first is a cell irradiation platform designed for cell culture plates and dishes, the first partition 13, the second partition 14, and located in the two partitions Between the stage 15 composition, the cell culture plate placed on the stage, a spacer 13 and the spacer 14 spacing of 12.9 cm, the stage height adjustable to ensure that the bottom of the cell culture plate is located in the irradiation area Middle position.

The specific magnetic field loading mode adopts the scheme as shown in FIG. 2, adopting a power frequency of 50/60 Hz, continuously changing the voltage through the DC and AC autotransformers, and generating the electromagnetic field superimposed on the DC and AC within the irradiated part through the following steps.

A specific voltage scheme in each time period T1-Tn to generate different magnetic field strengths in a total of eight time periods T1-T8 namely:

T1—a DC voltage of 3 mV, to generate a static electromagnetic field strength of 2.97 mT, an AC average voltage of 1.5 mV, to generate an average alternating magnetic field strength of 1.48 mT;

T2—a DC voltage of 4 mV to generate a static electromagnetic field strength of 3.95 mT, an AC average voltage of 2.5 mV, to generate an alternating magnetic field average strength of 2.47 mT;

T3—a DC voltage of 3 mV, to generate a static electromagnetic field strength of 2.97 mT, an AC average voltage of 1.5 mV, to generate an alternating magnetic field average strength of 1.48 mT;

T4—a DC voltage of 4 mV, to generate a static electromagnetic field strength of 3.95 mT, an AC average voltage of 2.5 mV, to generate an alternating magnetic field average strength of 2.47 mT;

T5—a DC voltage of 3 mV to generate a static electromagnetic field of 2.97 mT; an AC average voltage of 1 mV, to generate an alternating magnetic field average strength of 1.08 mT;

T6—a DC voltage of 4 mV into generate a static electromagnetic field strength of 3.95 mT, an AC average voltage of 1.5 mV, to generate an alternating magnetic field average strength of 1.48 mT;

T7—a DC voltage of 3 mV, to generate a static electromagnetic field strength of 2.97 mT, an AC average voltage of 1 mV, to generate an alternating magnetic field average strength of 1.08 mT;

T8—a DC voltage of 4 mV, to generate a static electromagnetic field strength of 3.95 mT, an AC average voltage of 1.5 mV, to generate an alternating magnetic field average strength of 1.48 mT.

The total magnetic field strength is the same at different positions within the irradiated region, the average magnetic field strength is 5.09 mT from T1 to T8; and each time the T1-Irradiation of the drug applied to the irradiated parts 8 of the object, the choice of platinum-based chemotherapeutic agents cisplatin, carboplatin, oxaliplatin, each round of irradiation time 30-90 minutes, 2-4 rounds per day irradiation, for cells And animal daily total irradiation time is 60-120 minutes. The subject selected cells or animals.

This example is a combination of drug selection cisplatin, its chemical formula well known.

Other platinum-based chemotherapeutic agents, including carboplatin, oxaliplatin and other therapeutic fields with the tumor, also belong to the scope of the patent protection.

Example 5, the present invention acts on cultured nephroblastoma cells G401, and the control group, the irradiation group, the cisplatin group and the combination group are respectively treated, and each treatment condition is three replicate wells, and the cells treated one day before are collected, Counted with a living cell counter, counted the number of cells according to the reading, and made a cell proliferation curve and an inhibition curve of the electromagnetic field to the cell.

The specific implementation process is as follows:

Cell Lines and Methods of Culture: Nephroblastoma cells G401, adherent cells, were cultured in McCoy's medium with 10% fetal bovine serum at 37° C. in an incubator containing 5% carbon dioxide and saturated water vapor.

Major equipment: power frequency electromagnetic field device, cell incubator, living cell counter.

Cell viability assay: G141 cells were seeded into 6-well plates at a density of $1 \times 10^5$ cells/well. The irradiation group was treated with the apparatus as shown in FIG. 1, and the cells were treated according to the protocol described in FIG. 4, Voltage for 3.5 minutes, the role of each round of about 30 minutes, 4 days a day, a total of 2 hours of electromagnetic field irradiation time; cisplatin group added cisplatin (Jiangsu Howson Pharmaceutical Co., Ltd.), the drug concentration of 500 nM, Administered once a day; combination group radiation and cisplatin combination of radiation loading mode and cisplatin administration and the same single-use group; control group cells placed in the electromagnetic field coil is not placed between the stage, 2 hours a day, and added with cisplatin group, the same volume of saline; daily collection of cells treated the day before, with live cell counter count, calculate the number of cells according to the reading, cell proliferation curve and electromagnetic field inhibition curve.

Statistical Analysis: Each irradiation conditions repeated three times, each three holes, the results were mean±standard error, the results do T test, with $P<0.05$ as a significant difference in indicators.

As shown in FIG. 5, the left panel shows the proliferation curve of G401 cells, wherein the X axis is the number of days of cell treatment, the Y axis is the number of cells, the curve one is the cell proliferation curve of the control group, the curve two is the cell proliferation curve of the irradiation group, Is the cell proliferation curve of cisplatin group, curve four is the cell proliferation curve of the combination group; the right graph is the cell inhibition curve, wherein the X axis is the cell treatment days, the Y axis is the cell inhibition rate (%), and the curve one is the irradiation group Cell inhibition curve, the second curve is the cisplatin cell inhibition rate curve, the third curve for the combination group cell inhibition rate curve; the results showed that radiation group, cisplatin group, combination group cells were slow proliferation, cell inhibition The rate of increase, of which the combined group of cells the slowest rate of cell proliferation, the highest inhibition rate.

In Example 6, the present invention acts on cultured neuroblastoma cells CHLA255, the control group, the irradiation group, the cisplatin group and the combination group separately, and each of the treatment conditions is three replicate wells, and the cells treated by the previous day are collected, Counted with a living cell counter, counted the number of cells according to the reading, and made a cell proliferation curve and an inhibition curve of the electromagnetic field to the cell.

The specific implementation process is as follows:

Cell Lines and Methods of Culture: Neuroblastoma cells, CHLA255, which are adherent cells, are grown in 37° C. incubator with 10% fetal calf serum in McCoy's medium containing 5% carbon dioxide and saturated water vapor.

Major equipment: power frequency electromagnetic field device, cell incubator, living cell counter.

Cell viability assay: Neuroblastoma cells, CHLA255, were seeded in 6-well plates at a density of $1 \times 10^5$ cells/well. The irradiation group was treated with the apparatus shown in FIG. 1, and the cells were treated according to the protocol described in FIG. 4, Voltage for 3.5 minutes, the role of each round of about 30 minutes, 4 days a day, a total of 2 hours of electromagnetic field irradiation time; cisplatin group added cisplatin (Jiangsu Howson Pharmaceutical Co., Ltd.), the drug concentration of 500 nM, Administered once a day; combination group radiation and cisplatin combination of radiation loading mode and cisplatin administration and the same single-use group; control group cells placed in the electromagnetic field coil is not placed between the stage, 2 hours a day, and added with cisplatin group, the same volume of saline; daily collection of cells treated the day before, with live cell counter count, calculate the number of cells according to the reading, cell proliferation curve and electromagnetic field inhibition curve.

Statistical Analysis: Each irradiation conditions repeated three times, each three holes, the results were mean±standard error, the results do T test, with P<0.05 as a significant difference in indicators.

As shown in FIG. 6, the left panel shows the proliferation curve of CHLA255 cells, wherein the X-axis is the number of days of cell treatment, the Y-axis is the number of cells, the curve one is the cell proliferation curve of the control group, the curve two is the cell proliferation curve of the irradiation group, Is the cell proliferation curve of cisplatin group, curve four is the cell proliferation curve of the combination group; the right graph is the cell inhibition curve, wherein the X axis is the cell treatment days, the Y axis is the cell inhibition rate (%), and the curve one is the irradiation group Cell inhibition curve, the second curve is the cisplatin cell inhibition rate curve, the third curve for the combination group cell inhibition rate curve; the results showed that radiation group, cisplatin group, combination group cells were slow proliferation, cell inhibition The rate of increase, of which the combined group of cells the slowest rate of cell proliferation, the highest inhibition rate.

Example 7: G401 nephroblastoma model was established in nude mice and the animals were randomly divided into 4 groups with 8 mice in each group. The control group, irradiation group, cisplatin group and combination group were treated respectively for 15 days The animals were sacrificed 3 days after the treatment, the tumor weights were weighed, and the biochemical indicators related to the blood analysis were taken to determine the hepatotoxicity of the drugs and irradiation.

Tumor models were established: Male nude mice were infants aged 3-4 weeks old. Nephroblastoma G401 was inoculated into the axilla and the number was $5 \times 10^6$/volume. The volume was 200 microliters. After one week of inoculation, the tumor could be touched. The animals were randomized groups, control group, irradiation group, cisplatin group, combined groups, treated separately.

Major equipment: low-frequency electromagnetic field device, animal irradiation platform, automatic biochemical analyzer (Beckman Coulter Au5800).

Tumor growth inhibition in vivo: nude mice were randomly divided into 4 groups, control group, irradiation group, cisplatin group, combined group, each group of 8, irradiation group according to the scheme shown in FIG. 4, each time to change the voltage effect 10 Minutes, each round of action time of about 90 minutes a day for a total of 14 days; cisplatin group was given cisplatin (Jiangsu Howson Pharmaceutical Co., Ltd.) 20 mg/kg, for three times a week, the rats in the control group were given cisplatin at the same time as the irradiation. The control animals were placed in the animals irradiated with electromagnetic field-free coils for 90 minutes every day, and injected intraperitoneally with the same volume of physiology Saline; all animals were sacrificed 3 days after the neck, the eyeball to take whole blood, EDTA anticoagulant, after centrifugation to take the biochemical indicators of blood plasma, remove underarm growth tumor, weighed tumor weight, tissue cryopreservation.

Statistical analysis: Each group of 8 animals, the results were mean±standard deviation, the results of T test, P<0.05 as a significant difference in indicators.

Figure 9:
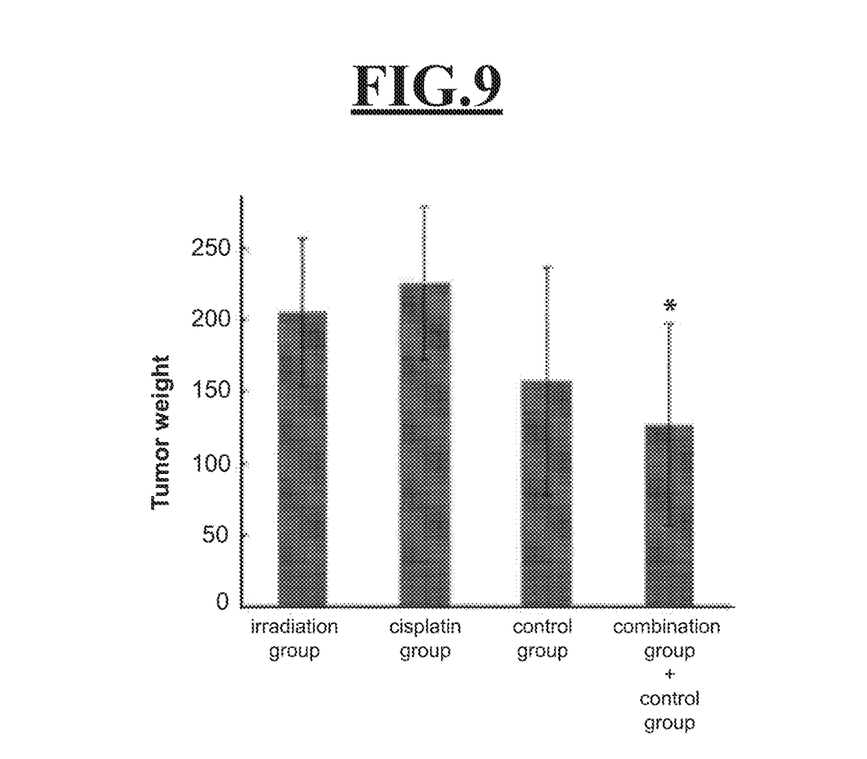
FIG. 9 is a graph showing the effect of the present invention on growth of nephroblastoma G401 in vivo.

As shown in FIG. 9, * indicates P<0.05, which is significantly different from that of the control group. Significant differences in tumor weight appear between the combination group and the control group, while the irradiation group, the cisplatin group and the control group There was no significant difference, indicating that radiation and cisplatin combination of growth inhibition of tumors in vivo is better than radiation or cisplatin alone.

Figure 10:
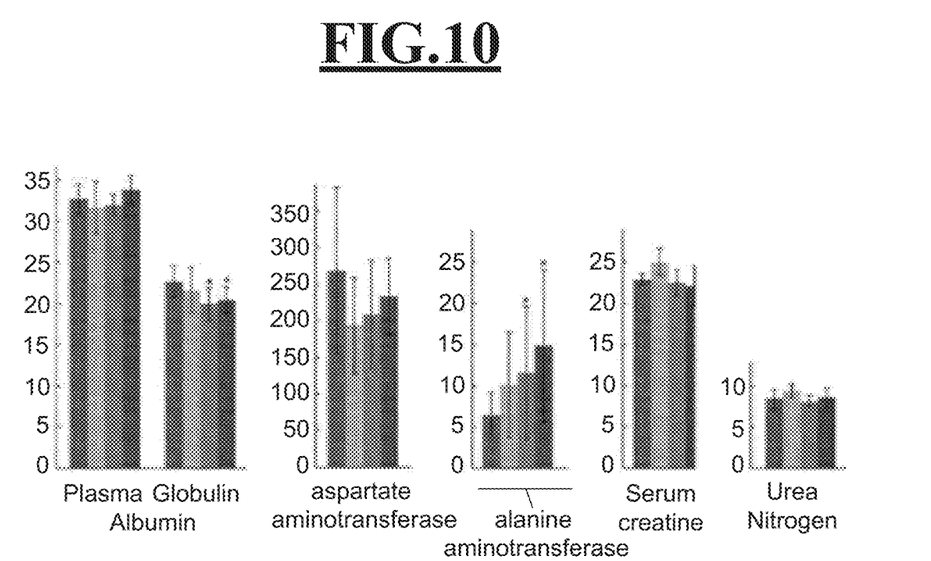
FIG. 10 shows the effect of the present invention on liver and kidney function of G401 mouse model of nephroblastoma.

As shown in FIG. 10, * indicates P<0.05, and there is a significant difference compared with the control group. Plasma albumin, globulin, aspartate aminotransferase, alanine aminotransferase, and serum creatinine reflecting renal function reflect liver function, Urea nitrogen in these indicators, only a plasma globulin, cisplatin group and combination group significantly lower than the control group, the change is mainly associated with cisplatin hepatotoxicity, and in the experiment using the electromagnetic field irradiation conditions, Found no animal liver and kidney damage, preliminary evidence of systemic toxicity of radiation is low. With reference to FIGS. 11 and 12, two different embodiments of the apparatus according to the invention are shown.

At least one coil can be provided, for example arranged in two separate coils 6 and 7 integrated in respective plates. It is possible that the patient represents all the workspace 8, or, alternatively, the patient moves relatively to the workspace, either translating the support or the coils 6,7.

The invention claimed is:
1. An apparatus for treating pathological cells, of neuroblastoma or nephroblastoma type, comprising:
a workspace configured to receive a target body,
at least one set of coils arranged to irradiate a static electromagnetic field in said workspace and also arranged to irradiate an alternating magnetic field in said workspace, and
control unit arranged to supply selectively currents to said at least one set of coils in such a way to irradiate in said workspace, said static electromagnetic field and said alternating magnetic field for predetermined time intervals T1-Tn, where n=whole number, said control unit configured to supply selectively said currents to said at least one set of coils in such a way to irradiate the pathologic cells, of neuroblasts or nephroblastoma type positioned within said workspace, said static electromagnetic field and said alternating magnetic field superimposed to each other with a maximum superimposed strength of 100 mT (milliTesla) and a ratio of the static electromagnetic field to the alternating magnetic field in the range of 0.5-2.5, said static electromagnetic field having an intensity selected in such a way that said static electromagnetic field and said alternating magnetic field superimposed to each other have always a strength with a positive value, wherein:
said control unit is arranged to keep in said workspace a total magnetic field obtained by said static electromagnetic field and said alternating magnetic field superimposed to each other at a uniform same overall strength within entire volume of said workspace, said overall strength comprised within a range of 1.0-7.0 mT, or said overall strength is between 4 and 6 mT, or said overall strength is between 4.5-5.5 mT, or said overall strength is 5.1 mT,
said control unit is configured to supply selectively current to said set of coils in each of said time intervals T1-Tn according to a predetermined voltage scheme, according to which in each time interval T1-Tn a DC (Direct Current) voltage is applied to said set of coils in a voltage range of 1-5 mV (milliVolt) to generate a static electromagnetic field strength range of 1-5 mT, and an AC (Alternate Current) voltage is applied to said set of coils in an average voltage range of 1-5 mV to generate the alternating magnetic field with an average strength range of 1-5 mT, and the control unit is configured to set a duration of the magnetic field each time a voltage of said voltage scheme is changed for each time interval T1-Tn in such a way that an electromagnetic irradiation is continued for 3.5-10 minutes and an irradiation time per each T1-Tn rotation is 30-90 minutes, wherein the control unit is configured to apply said voltage scheme in each time interval T1-Tn to generate different magnetic field strengths in a total of eight time periods T1-T8 namely:

T1—a DC voltage of 3 mV, to generate a static electromagnetic field strength of 2.97 mT, an AC average voltage of 1.5 mV, to generate an average alternating magnetic field strength of 1.48 mT;

T2—a DC voltage of 4 mV to generate a static electromagnetic field strength of 3.95 mT, an AC average voltage of 2.5 mV, to generate an alternating magnetic field average strength of 2.47 mT;

T3—a DC voltage of 3 mV, to generate a static electromagnetic field strength of 2.97 mT, an AC average voltage of 1.5 mV, to generate an alternating magnetic field average strength of 1.48 mT;

T4—a DC voltage of 4 mV, to generate a static electromagnetic field strength of 3.95 mT, an AC average voltage of 2.5 mV, to generate an alternating magnetic field average strength of 2.47 mT;

T5—a DC voltage of 3 mV to generate a static electromagnetic field of 2.97 mT; an AC average voltage of 1 mV, to generate an alternating magnetic field average strength of 1.08 mT;

T6—a DC voltage of 4 mV, into generate a static electromagnetic field strength of 3.95 mT, an AC average voltage of 1.5 mV, to generate an alternating magnetic field average strength of 1.48 mT;

T7—a DC voltage of 3 mV, to generate a static electromagnetic field strength of 2.97 mT, an AC average voltage of 1 mV, to generate an alternating magnetic field average strength of 1.08 mT; and T8—a DC voltage of 4 mV, to generate a static electromagnetic field strength of 3.95 mT, an AC average voltage of 1.5 mV, to generate an alternating magnetic field average strength of 1.48 mT.

2. The apparatus according to claim 1, wherein said set of coils is selected from the group consisting of:

a single set of coils in which a voltage supply is applied superimposing a static DC supply and an alternating AC supply, and a first set of coils arranged to irradiate said static electromagnetic field in said workspace and a second set of coils arranged to irradiate said alternating magnetic field in said workspace.

3. The apparatus according to claim 1, wherein a total irradiation time is 60-180 minutes for two rotations of T1-Tn.

4. The apparatus according to claim 1, wherein an AC supply for providing the alternating electromagnetic field has a frequency of 50-60 Hz.

5. The apparatus according to claim 1, wherein a further AC supply is provided to cause an alternating magnetic signal in said at least one coil, said further AC supply being superimposed to the static electromagnetic field and to the alternating magnetic field, said further AC supply having a frequency between 1 Hz and 100 MHz and an intensity between 1 microTesla (µT) and 100 mT.

6. The apparatus for irradiating a power frequency electromagnetic field, according to claim 1 in combination with a treatment of subministration of a platinum-based medicine.

7. The apparatus according to claim 6, wherein said platinum-based chemotherapeutic agents is selected from the group comprised of cisplatin, carboplatin and oxaliplatin.

8. The apparatus according to claim 1, wherein a total daily irradiation time is 60-120 minutes for cells and animals.

9. An apparatus for treating pathological cells, of neuroblastoma or nephroblastoma type, comprising:

a workspace configured to receive a target body, at least one set of coils arranged to irradiate a static electromagnetic field in said workspace and also arranged to irradiate an alternating magnetic field in said workspace, and control unit arranged to supply selectively currents to said at least one set of coils in such a way to irradiate in said workspace, said static electromagnetic field and said alternating magnetic field for predetermined time intervals T1-Tn, where n=whole number, said control unit configured to supply selectively said currents to said at least one set of coils in such a way to irradiate the pathologic cells, of neuroblasts or nephroblastoma type positioned within said workspace, said static electromagnetic field and said alternating magnetic field superimposed to each other with a maximum superimposed strength of 100 mT (milliTesla) and a ratio of the static electromagnetic field to the alternating magnetic field in the range of 0.5-2.5, said static electromagnetic field having an intensity selected in such a way that said static electromagnetic field and said alternating magnetic field superimposed to each other have always a strength with a positive value, wherein:

said control unit is arranged to keep in said workspace a total magnetic field obtained by said static electromagnetic field and said alternating magnetic field superimposed to each other at a uniform same overall strength in within entire volume of said workspace, said overall strength comprised within a range of 1.0-7.0 mT, or said overall strength is between 4 and 6 mT, or said overall strength is between 4.5-5.5 mT, or said overall strength is 5.1 mT, said control unit is configured to supply selectively current to said set of coils in each of said time intervals T1-Tn according to a predetermined voltage scheme, according to which in each time interval T1-Tn a DC (Direct Current) voltage is applied to said set of coils in a voltage range of 1-5 mV (milliVolt) to generate a static electromagnetic field strength range of 1-5 mT, and an AC (Alternate Current) voltage is applied to said set of coils in an average voltage range of 1-5 mV to generate the alternating magnetic field with an average strength range of 1-5 mT, and the control unit is configured to set a duration of the magnetic field each time a voltage of said voltage scheme is changed for each time interval T1-Tn in such a way that an electromagnetic irradiation is continued for 3.5-10 minutes and an irradiation time per each T1-Tn rotation is 30-90 minutes, wherein the apparatus is configured to provide to irradiated parts a combination treatment of a power frequency electromagnetic field generating device and a treatment with a platinum-based chemotherapeutic agent realized by the following steps:
constructing a power frequency electromagnetic field generating device,
adopting a power supply at a frequency of 50/60 Hz, continuously changing the voltage through a direct current and alternating current auto-transformers, creating the static electromagnetic field and the alternating magnetic field superimposed to each other within said irradiated parts with an average magnetic field of 1-7 millitesla and a total irradiation time of 60-120 minutes per day for the irradiated parts, wherein:
a supply is provided on the irradiated parts under exposure of a dose of platinum-based chemotherapeutic agents comprising:
in vitro concentration of 500 nM, once a day dosing, dose ratio of 20 mg/kg, administered three times a week;
the power frequency electromagnetic field generating device is composed of a power frequency power supply, a first autotransformer, a second autotransformer, a first diode bridge, a second diode bridge, a first set of coils, a second set of coils, an irradiating member, a voltage detecting member, a magnetic field detecting member, a temperature measuring member, a computer,
the power frequency power supply is respectively connected with the first autotransformer and the second autotransformer,
ends of the first autotransformer and of the second autotransformer are respectively connected with the first diode bridge and the second diode bridge,
a first end of the diode bridge is connected to the first set of coils and another end of the second diode bridge is connected to the second set of coils,
one end of the voltage detection component is respectively connected with the first group of coils and the second group of coils, and another end of the voltage detection component is connected with the computer,
the computer is connected with a magnetic field detecting part and a temperature measuring part, and
each of the magnetic field detecting part and the temperature measuring part are respectively connected with one end to the irradiated part and with the another end to the computer, respectively.

10. The apparatus according to claim 9, wherein said platinum-based chemotherapeutic agents is selected from the group comprised of cisplatin, carboplatin and oxaliplatin.

11. An apparatus for treating pathological cells, of neuroblastoma or nephroblastoma type, comprising:
a workspace configured to receive a target body,
at least one set of coils arranged to irradiate a static electromagnetic field in said workspace and also arranged to irradiate an alternating magnetic field in said workspace, and
control unit arranged to supply selectively currents to said at least one set of coils in such a way to irradiate in said workspace, said static electromagnetic field and said alternating magnetic field for predetermined time intervals T1-Tn, where n=whole number, said control unit configured to supply selectively said currents to said at least one set of coils in such a way to irradiate the pathologic cells, of neuroblasts or nephroblastoma type positioned within said workspace, said static electromagnetic field and said alternating magnetic field superimposed to each other with a maximum superimposed strength of 100 mT (milliTesla) and a ratio of the static electromagnetic field to the alternating magnetic field in the range of 0.5-2.5, said static electromagnetic field having an intensity selected in such a way that said static electromagnetic field and said alternating magnetic field superimposed to each other have always a strength with a positive value, wherein:
said control unit is arranged to keep in said workspace a total magnetic field obtained by said static electromagnetic field and said alternating magnetic field superimposed to each other at a uniform same overall strength within entire volume of said workspace, said overall strength comprised within a range of 1.0-7.0 mT, or said overall strength is between 4 and 6 mT, or said overall strength is between 4.5-5.5 mT, preferably or said overall strength is 5.1 mT,
said control unit is configured to supply selectively current to said set of coils in each of said time intervals T1-Tn according to a predetermined voltage scheme, according to which in each time interval T1-Tn a DC (Direct Current) voltage is applied to said set of coils in a voltage range of 1-5 mV (milliVolt) to generate a static electromagnetic field strength range of 1-5 mT, and an AC (Alternate Current) voltage is applied to said set of coils in an average voltage range of 1-5 mV to generate the alternating magnetic field with an average strength range of 1-5 mT, and
the control unit is configured to set a duration of the magnetic field each time a voltage of said voltage scheme is changed for each time interval T1-Tn in such a way that an electromagnetic irradiation is continued for 3.5-10 minutes and an irradiation time per each T1-Tn rotation is 30-90 minutes,
wherein the apparatus includes a combination of power frequency electromagnetic field generating device and platinum-based chemotherapeutic agents supply, and arranged to provide the following steps: using frequency from 1 Hz to 100 MHz and strength from 1 μT to 100 mT so as to generate superimposed static and alternating magnetic fields within irradiated components in said workspace, wherein a specific voltage scheme is applied to supply selectively said currents to said at least one set of coils to generate magnetic field strengths as follows, divided into time periods T1-T8 as follows:
T1—DC voltage of 3 mV to generate a static electromagnetic field strength of 2.97 mT, average AC voltage of 1.5 mV to generate an average alternating magnetic field strength of 1.48 mT;
T2—DC voltage of 4 mV to generate a static electromagnetic field strength of 3.95 mT, average AC voltage of 2.5 mV to generate an average alternating magnetic field strength of 2.47 mT;
T3—DC voltage of 3 mV to generate a static electromagnetic field strength of 2.97 mT, average AC voltage of 1.5 mV to generate an average alternating magnetic field strength of 1.48 mT;
T4—DC voltage of 4 mV to generate a static electromagnetic field strength of 3.95 mT, average AC voltage of 2.5 mV, to generate an average alternating magnetic field strength of 2.47 mT;
T5, DC voltage of 3 mV to generate a static electromagnetic field strength of 2.97 mT, average AC voltage of 1 mV to generate an average alternating magnetic field strength of 1.08 mT;

T6—DC voltage of 4 mV in, to generate a static electromagnetic field strength of 3.95 mT, average AC voltage of 1.5 mV to generate average alternating magnetic field of 1.48 mT;

T7—DC voltage of 3 mV to generate, a static electromagnetic field strength of 2.97 mT, average AC voltage of 1 mV, to generate an average alternating magnetic field strength of 1.08 mT; and T8—DC voltage of 4 mV to generate a static electromagnetic field strength of 3.95 mT, average AC voltage of 1.5 mV, to generate an average alternating magnetic field strength of 1.48 mT.

12. The apparatus according to claim 11, wherein said platinum-based chemotherapeutic agents are selected from the group comprised of cisplatin, carboplatin and oxaliplatin.

* * * * *